(12) United States Patent
Kimler et al.

(10) Patent No.: US 9,220,272 B2
(45) Date of Patent: Dec. 29, 2015

(54) ACTIVE HALOGEN ANTIMICROBIAL COMPOSITION AND METHOD OF USE

(71) Applicant: Lonza, Inc., Allendale, NJ (US)

(72) Inventors: Joseph Kimler, Yardville, NJ (US); Steven J. Colby, New Providence, NJ (US); Philip Gerdon Sweeny, Alpharetta, GA (US)

(73) Assignee: LONZA, INC, Allendale, NJ (US)

( * ) Notice: Subject to any disclaimer, the term of this patent is extended or adjusted under 35 U.S.C. 154(b) by 0 days.

(21) Appl. No.: 13/826,828

(22) Filed: Mar. 14, 2013

(65) Prior Publication Data

US 2013/0280349 A1    Oct. 24, 2013

Related U.S. Application Data

(60) Provisional application No. 61/637,075, filed on Apr. 23, 2012, provisional application No. 61/709,784, filed on Oct. 4, 2012.

(51) Int. Cl.
*A01N 59/00*    (2006.01)

(52) U.S. Cl.
CPC ...................... *A01N 59/00* (2013.01)

(58) Field of Classification Search
CPC ....................................... A01N 1/00
See application file for complete search history.

(56) References Cited

U.S. PATENT DOCUMENTS

2005/0124519 A1*  6/2005  Sherry et al. .................. 510/238
2012/0114632 A1*  5/2012  Janak et al. .................... 424/126

FOREIGN PATENT DOCUMENTS

| EP | 1236398 A1 | 9/2002 |
| GB | 2078522 A | 1/1982 |
| WO | 99/32596 A1 | 7/1999 |
| WO | WO2004/026770 * | 4/2004 |

OTHER PUBLICATIONS

Dr France 2014 http://www.gcsescience.com/aa24.htm.*
Sliwa, Jim: "Vinegar increases killing power of bleach", EurekAlert!, Feb. 17, 2006, Retrieved from the Internet: URL: http://www.eurekalert.org/pub_releases/2006-02/asfm-vik021306.php [retrieved on Jul. 16, 2013]; the whole document.

* cited by examiner

*Primary Examiner* — Scott Long
*Assistant Examiner* — Sarah Alawadi
(74) *Attorney, Agent, or Firm* — Lucas & Mercanti LLP

(57) ABSTRACT

Disclosed is an antimicrobial composition containing an active halogen-containing component having a source of an active halogen and having an elevated pH, which is mixed with an acidic component. An acidic component is added in an amount to the active halogen-containing component to reduce the pH of the antimicrobial composition. When the pH of the active halogen-containing composition is reduced, the resulting composition has been discovered to be effective as a disinfectant and, particularly, as a sporicide. Application methods for applying the composition are also described.

29 Claims, No Drawings

ACTIVE HALOGEN ANTIMICROBIAL COMPOSITION AND METHOD OF USE

CROSS-REFERENCE TO RELATED APPLICATIONS

This application claims priority under 35 U.S.C §119(e) from U.S. Ser. No. 61/709,784 filed Oct. 4, 2012, entitled "Active Halogen Antimicrobial Composition"; and U.S. Ser. No. 61/637,075, filed Apr. 23, 2012, entitled "Stabilized Halogen Disinfectant Composition". The disclosure of both U.S. Ser. No. 61/709,784 and U.S. Ser. No. 61/637,075 are incorporated herein by reference in their entirety.

FIELD OF THE INVENTION

The present invention relates to an antimicrobial composition which is effective in decontaminating surfaces, delivery methods for applying the antimicrobial composition to the surface, and the method of decontaminating those surfaces.

BACKGROUND OF THE INVENTION

Antimicrobial compositions for decontamination, disinfection and/or sanitization must have an effective microbial kill rate to be suitable for use as decontamination, disinfection and/or sanitization compositions. These antimicrobial compositions are generally desirable to be low in corrosion to the surfaces being treated and to be low in odor. In addition, these compositions generally will only contain enough of the microbial control agent to be effective for a given application. Having too much of the microbial control agent does not provide any advantages to the resulting composition, essentially wasting any excess microbial control agent in the composition. Having too little microbial control agent will make the composition less than effective than needed for its intended use.

Stabilized active halogen solutions have been used for the treatment of recirculated industrial cooling waters and are known in the art. Such products are typically used as-provided and applied at relatively low concentrations to achieve biocidal control of vegetative microbiological species in the recirculated water. Examples of stabilized active halogen solutions include Stabrex® from Nalco Inc., which is generally described in U.S. Pat. Nos. 5,942,126; 6,007,726; 5,683,654; 6,123,870; 6,136,205; 6,669,904; 6,660,307; 6,423,267; 6,156,229; BromMax® from Enviro Tech Chemicals, which is generally described in U.S. Pat. Nos. 7,045,153; 7,309,503; and 7,045,153; and Stabrom® from Albemarle, which is generally described in U.S. Pat. Nos. 6,068,861; 6,299,909; 6,306,441; 6,322,822; 6,652,889; 6,551,624; 6,511,682; 6,506,418; 6,495,169; 6,375,991; 6,352,725; 6,348,219; and 6,322,822. Each of these patents is incorporated herein by reference in its entirety. Another commercially available stabilized halogen-containing solution includes Justeq, available from Justeq, LLC, Northbrook, Ill. These solutions typically contain a bromine stabilizer, such as sulfamic acid, and a source of active bromine and are generally provided to the user at elevated pH. The solutions are applied at a relatively low concentration, generally less than about 100 ppm of product, which generally translates to less than 10 ppm active halogen as $Cl_2$. These low application rates are insufficient to significantly alter the system pH, and the thus observed efficacy is that associated with the low level active halogen applications at an elevated pH. Such utility is insufficient to achieve hard surface disinfection, sanitation or sporicidal performance targets.

*Clostridium difficile*, commonly called *C. diff*, is one of the major causes of HAIs (Hospital Acquired Infections). The difficulty in controlling *C. diff.* results from the durability of the spore form. Since *C. diff* spores are difficult to deactivate and kill, relatively high concentrations of aggressive disinfectants are required to control outbreaks when they occur. Chlorine bleach (sodium hypochlorite) and peracetic acid compositions at relatively high concentrations are examples of disinfectants used that are effective against *C. diff.* spores. However, both chlorine bleach and peracetic acid compositions present significant environmental and handling drawbacks, most notably, but not limited to, strong odors that are considered to be noxious to most humans.

There is a need in the art for a disinfecting composition that will be effective in controlling *C. diff* spores without the drawbacks of chlorine bleach and peracetic acid containing compositions, as noted above.

SUMMARY OF THE INVENTION

It has been discovered that active halogen-containing compositions may be modified to form compositions which achieve sufficient efficacy for sanitizing, disinfecting and sporicidal applications and may additionally provide more favorable handling characteristics, such as reduced odor.

Provided herein is an antimicrobial composition contains an active halogen-containing component and an acidic component. Generally, the active halogen-containing component will have an elevated pH (typically above a pH of 9). The acidic component is added to the active halogen-containing component in an amount sufficient to reduce the pH of the antimicrobial composition to a value lower than about 8. When the pH of the active halogen-containing component containing composition is reduced, the resulting antimicrobial composition has been discovered to be effective as a disinfectant and, particularly, as a sporicide.

In another aspect, the active halogen in the active halogen-containing component may be any halogen, but is typically active chlorine, active bromine or active iodine. Of these active halogens, active bromine is of the most interest.

In further aspect, the active halogen-containing component contains an active halogen source derived a compound selected from the group consisting of bromine, bromine chloride, halogenated cyanurate, alkaline earth metal hypohalites, alkali metal hypohalites, chlorine gas, a halogenated hydantoin and mixtures thereof.

In the antimicrobial composition, the acidic component may be a strong acid selected from the group consisting of hydrochloric acid, nitric acid, phosphoric acid, sulfuric acid, and sulfamic acid; a partial salt of a strong acid selected from the group consisting of bisulfates, and dihydrogen phosphates; a weak acid selected from the group consisting of lactic acid, tartaric acid, citric acid, oxalic acid, glucolic acid, acetic acid, ascorbic acid, carbonic acid, salicylic acid, benzoic acid, maleic acid, succinic acid, gluconic acid, adipic acid and boric acid; a partial salt of a weak acids selected from the group consisting of bicarbonates, citrates, tartates, oxalates, glucolates, acetates, ascorbates, salicylates, benzoates, maleates, succinates, gluconates, adipates, and borates; a combination of a strong acid and a weak acid or a partial salt of a weak acid; and the combination of a strong acid and a partial salt of a strong acid.

In another aspect, the acidic component is added to the composition in an amount to reduce the pH of the antimicrobial composition to a pH of 7.0 or below, typically to a pH of 6.0 or below, more typically a pH of 4.0 or below and most typically to a pH of 3.0 or below. In one aspect, the acidic component may have a pH of below 3.

In an additional aspect, the antimicrobial composition may further contain a stabilizer. Suitable stabilizers include compounds that have N—H groups. One exemplary stabilizer is sulfamic acid. The stabilizer may be added to the active halogen-containing component or to the acid component.

In a further aspect, the antimicrobial composition will have concentration of the total active halogen in the resulting antimicrobial composition should generally be in the range between about 25 ppm and about 60,000 ppm, based on the total weight of the antimicrobial composition, on a $Cl_2$ equivalent basis. More typically, the total active halogen in the resulting antimicrobial composition will be in the range between about 50 ppm and 12,000 ppm, on a $Cl_2$ equivalent basis. Most typically, the total active halogen in the resulting composition will be in the range of about 500 ppm and 10,000 ppm, on a $Cl_2$ equivalent basis. For example, the total active halogen in the composition may be in the range of about 1000 ppm to about 9000 ppm and more typically between about 4,000 ppm and 8,000 ppm, on a $Cl_2$ equivalent basis. Other suitable ranges may also be used, for example in the range of about 5000 ppm to about 7000 ppm.

In a further aspect, the antimicrobial compositions contains the active halogen-containing component which is an active halogen source selected from the group consisting of bromine, bromine chloride, chlorinated cyanurate, calcium hypochlorite, chlorine gas, sodium hypochlorite, sodium hypobromite, lithium hypochlorite, lithium hypobromite, a halogenated hydantoin and mixtures thereof; and an acidic component is a strong acid selected from the group consisting of hydrochloric acid, phosphoric acid, sulfuric acid, and sulfamic acid; a partial salt of a strong acid selected from the group consisting of bisulfates, and dihydrogen phosphates; a weak acid selected from the group consisting of lactic acid, tartaric acid, citric acid, oxalic acid, glucolic acid, acetic acid, ascorbic acid, carbonic acid, salicylic acid, benzoic acid, maleic acid, succinic acid, gluconic acid, adipic acid and boric acid; a partial salt of a weak acid selected from the group consisting of bicarbonates, citrates, tartates, oxalates, glucolates, acetates, ascorbates, salicylates, benzoates, maleates, succinates, gluconates, adipates, and borates; a combination of a strong acid and a weak acid or a partial salt of a weak acid; and the combination of a strong acid and a partial salt of a strong acid. The composition further contains an N—H containing compound as a stabilizer. The total active halogen concentration in the composition is between about 500 and 10,000 ppm on a $Cl_2$ equivalent basis and in particular the total active halogen concentration in the composition is between about 4000 and 8,000 ppm on a $Cl_2$ equivalent basis.

Also provided is a stable two-part antimicrobial composition having a first part which contains an active halogen-containing component having a source of an active halogen and having an elevated pH. The second part contains an acidic component. The first and second parts of the composition are kept separate from each other during storage and prior to use. The first part and the second part are mixed together just prior to use to obtain an antimicrobial composition. By having the two parts separated prior to use, the active halogen remains stable and active during storage of the composition prior to use. In addition, once mixed, the resulting antimicrobial composition can be stored for a defined period of time after mixing, while remaining effective. When the first part is mixed with the second part, the resulting antimicrobial composition has been discovered to be effective as a disinfectant and, particularly, as a sporicide.

In another aspect, the active halogen in the active halogen-containing component of the two-part composition may be any halogen, but is typically active chlorine, active bromine or active iodine. Of these active halogens, active bromine is of the most interest.

In further aspect, the active halogen-containing component of the two-part composition contains an active halogen source derived a compound selected from the group consisting of bromine, bromine chloride, chlorinated cyanurate, calcium hypochlorite, chlorine gas, sodium hypochlorite, sodium hypobromite, lithium hypochlorite, lithium hypobromite, a halogenated hydantoin and mixtures thereof.

In the antimicrobial composition, the acidic component of the two-part composition may be a strong acid selected from the group consisting of hydrochloric acid, nitric acid, phosphoric acid, sulfuric acid, and sulfamic acid; a partial salt of a strong acid selected from the group consisting of bisulfates, and dihydrogen phosphates; a weak acid selected from the group consisting of lactic acid, tartaric acid, citric acid, oxalic acid, glucolic acid, acetic acid, ascorbic acid, carbonic acid, salicylic acid, benzoic acid, maleic acid, succinic acid, gluconic acid, adipic acid and boric acid; a partial salt of a weak acids selected from the group consisting of bicarbonates, citrates, tartates, oxalates, glucolates, acetates, ascorbates, salicylates, benzoates, maleates, succinates, gluconates, adipates, and borates; a combination of a strong acid and a weak acid or a partial salt of a weak acid; and the combination of a strong acid and a partial salt of a strong acid.

In another aspect, the acidic component of the two-part composition is added to the first part in an amount to reduce the pH of the resulting antimicrobial composition to a pH of 7.0 or below, typically to a pH of 6.0 or below, more typically a pH of 4.0 or below and most typically to a pH of 3.0 or below. In one aspect, the acidic component may have a pH of below 3. In addition, the acidic component may contain a bromine containing compound as the source of bromine in the two-part antimicrobial composition.

In an additional aspect, the two-part antimicrobial composition may further contain a stabilizer. The stabilizer may be present in the first part, or the second part, or both the first and second parts. Suitable stabilizers include compounds that have N—H groups. One exemplary stabilizer is sulfamic acid. The stabilizer may be added to the active halogen-containing component or to the acid component.

In yet another aspect of the present invention, two-part composition may be provided the end user in various ways. The first part is provided in a first container and the second part is provided in second container and the amount of the first part in the first container and the amount of the second part in the second container are proportional such that the entire contents of both containers are mixed together to form an antimicrobial composition. Alternatively, the first part and the second part are in a single container, wherein the first part is separated from the second part in the container by a separator. The separator may be removable from the container or movable in the container to allow the first part and the second part can mix together in the container. In another embodiment, the container further have a spray head and the first part and the second part are mixed in the spray head as the composition is applied to the surface to be treated. In yet another embodiment, the first part and the second part are provided in containers where a portion of the first part and a portion of the second part from each container are mixed together.

In addition, a diluent may be added any of the above-described or herein-described antimicrobial compositions to reduce the concentration of the active halogen into a desired concentration range.

The antimicrobial composition may also be saturated into a wipe and the wipe may be used to apply any of the above-described or herein-described antimicrobial composition to a surface to be treated. Alternatively, the antimicrobial composition may be in the form of a liquid that is sprayed, poured or otherwise applied onto a surface to be treated with the antimicrobial composition.

Also provided is a method of disinfecting a surface, which includes applying any of the above-described or herein-described antimicrobial composition to the surface. In addition, provided is a method of controlling spores on a surface. In this method, any of the above-described or herein-described antimicrobial compositions is applied to the surface.

DETAILED DESCRIPTION OF THE INVENTION

The present invention, generally stated, relates to an antimicrobial composition containing active halogen-containing component and an acidic component. It has been discovered that the acidic component enhances the activity of the active halogen containing component in the antimicrobial composition when the antimicrobial composition has a pH of 8 or less.

It has been discovered that lowering the pH of an active halogen-containing component or solution containing the active halogen-containing component by the addition of an acidic component to adjust the pH level to about 8 or less, the resulting acidified active halogen-containing antimicrobial composition has an improved antimicrobial efficacy, and, particularly results in a composition having sporicidal efficacy. As such, the antimicrobial composition described herein is especially effective as a disinfectant composition used to kill *C. diff.* spores. Not only does the acidified active halogen-containing antimicrobial composition achieve enhanced efficacy desired for sporicidal applications, the acidified active halogen-containing antimicrobial composition can also have additional advantages of having reduced odor, as compared to currently available sporicidal compositions.

The active halogen-containing component usable in the present invention may be derived from halogen sources including active chlorine, bromine, or iodine. Generally, the active halogen will contain at least active bromine as the active halogen; however the other halogens may be used. Typically, the active halogen-containing component is prepared from a source of an active halogen, such as bromine; bromine chloride; halogenated cyanurates; such as chlorinated cyanurates (mono chlor, dichlor and trichlor); halogenated cyanuric acid; alkaline earth metal hypohalites such as, calcium hypochlorite; chlorine gas; alkali metal hypohalites such as, sodium hypochlorite, sodium hypobromite, lithium hypochlorite, lithium hypobromite; halogenated hydantoins, and the like. It is also possible to use more than one of these active halogen-containing components as a source of the halogen. Alternatively, bromine in the composition may be derived from a bromine-containing compound which is added to the composition containing an active chlorine-containing compound. The bromine source may be derived from a bromine compound such as sodium bromide, potassium bromide and other similar bromine containing compounds. When these bromine compounds are added, the bromide is activated to form active bromine by another source of active halogen in the composition, for example, active chlorine. Generally, bromine has advantages over chlorine in that bromine typically has a less offensive odor as compared to chlorine. Also it has been discovered that bromine has superior efficacy in the presence of a nitrogenous substances, as described herein.

The active halogen-containing component is generally in a solution with the active halogen-containing component dissolved in the solution. Generally, the active halogen solution will have an elevated pH. By "elevated pH" it is intended that the solution has a pH in the basic range, typically above a pH of about 9.0. Active halogen solutions need to have an elevated pH to provide acceptable stability of the solution during production and storage. Not wishing to be bound by theory, but it is believed that the elevated pH minimizes the formation of the acid forms of the contained hypohalites, thus slowing the disproportionation reaction of the acid forms, which is generally the primary route of decomposition. As such, active halogen-containing solutions thus are prepared at elevated pH, typically a pH greater than about 10.0 or more, so that the active halogen compound does not dissipate. Generally, at lower pH's the active halogen in solution will dissipate making the composition less effective.

Generally, to form the active halogen-containing solution, first an elevated pH solution is formed. This elevated pH solution is generally prepared by adding a basic component, such as sodium hydroxide to an aqueous solution. Other basic materials may be used to prepare the elevated pH solution without departing from the scope of the present invention. The active halogen source is added to the elevated pH solution which results in the active halogen-containing solution having an elevated pH. Other methods known in the art to form halogen-containing solutions may also be used. The active halogen-containing solution will generally be a concentrated halogen-containing solution, having a halogen content well above the typical concentration needed for disinfecting. Typically, the pH of the active halogen-containing solution is above about 9.0, more typically above 9.5, and most typically about 10.0 or above. At these elevated pH's, the active halogen-containing component is stabilized in the solution by the addition of a stabilizer, which is described in more detail below.

To form the antimicrobial composition of the present invention, an acidic component is added to the active halogen-containing component. The acid serves to reduce the pH of the active halogen-containing component so that the active halogen-containing component in solution can be made useful as a disinfectant. Suitable acidic components include both strong acids, partial salts of strong acids, weak acids, partial salts of weak acids and mixtures thereof. Suitable strong acids include, but are not limited to, hydrochloric acid, nitric acid, phosphoric acid, sulfuric acid, and sulfamic acid. Suitable partial salts of strong acids include bisulfates, and dihydrogen phosphates partial salts, including, but are not limited to, sodium bisulfate, sodium dihydrogen phosphate and potassium dihydrogen phosphate. Suitable weak acids, include, but are not limited to, lactic acid, tartaric acid, citric acid, oxalic acid, glucolic acid, acetic acid, ascorbic acid, carbonic acid, salicylic acid, benzoic acid, maleic acid, succinic acid, gluconic acid, adipic acid and boric acid. Suitable partial salts of weak acids include, but not limited to, bicarbonates, citrates, tartates, oxalates, glucolates, acetates, ascorbates, salicylates, benzoates, maleates, succinates, gluconates, adipates, borates and the like. The salts may be sodium salts, potassium salts, calcium salts, magnesium salts and the like. An exemplary partial salt of a weak acid includes, but not limited to, sodium bicarbonate. In addition mixtures of these acids may be used as the acidic component of the antimicrobial composition.

The acidic component is added to the active halogen-containing solution to form the antimicrobial composition. The acid component is added in an amount to form an antimicrobial solution having a pH which is about 8 or lower. Generally, the acidic component is added to the active halogen-containing solution to form an antimicrobial composition which has a pH of about 7 or below, and more particularly a pH of about 6 or below. The pH of the solution can be even lower, for example, a pH of about 4 or below. The pH of the solution can be still even lower, for example, a pH of about 3 or below Again, the pH is adjusted by adding the acidic component.

In addition to the lowering the pH of the active halogen-containing solution, it may also be necessary to lower the concentration of the active halogen-containing component in the resulting disinfectant. The concentration of the total active halogen in the resulting antimicrobial composition should generally be in the range between about 25 ppm and about 60,000 ppm, based on the total weight of the antimicrobial composition, on a $Cl_2$ equivalent basis. Concentrations above about 60,000 ppm, may be used in the present invention. More typically, the total active halogen in the resulting antimicrobial composition will be in the range between about 50 ppm and 12,000 ppm, on a $Cl_2$ equivalent basis. Most typically, the total active halogen in the resulting composition will be in the range of about 500 ppm and 10,000 ppm, on a $Cl_2$ equivalent basis. For example, the total active halogen in the composition may be in the range of about 1000 ppm to about 9000 ppm and more typically between about 4,000 ppm and 8,000 ppm, on a $Cl_2$ equivalent basis. Other suitable ranges may also be used, for example in the ranges of about 5000 ppm to about 7000 ppm. Active halogen as $Cl_2$ can be measured using methods know to those skilled in the art, for example by thiosulfate titration and colorimetric N,N-diethyl-p-phenylenediamine (DPD).

In the present invention, it is beneficial if either the acidic component or the active halogen-containing component contains a stabilizer moiety or a stabilizer additive to safely prepare the antimicrobial composition. Suitable stabilizer compounds, which are classified as N-hydrogen compounds, include essentially any compound that stabilizes or complexes the active halogen in solution. N-hydrogen compounds are compounds which have an N—H group which is free to react and complex with active halogens. Exemplary classes of compounds include, for example, ammonium compound, sulfonamides, hydantoins, urea compounds, cyanuric compounds, oxizolidinone compounds and other similar compounds. Specific examples include ammonium compounds, including but not limited to ammonium sulfate, ammonium chloride, ammonium carbonate, ammonium bromide; methanesulfonamide, glycoluril, dimethyl hydantoin, methyl ethyl hydantoin, urea, cyanuric acid and other similar compounds. Other suitable stabilizers include the stabilizers or mixtures, such as the mixtures described in US Patent Application Publication US 2012/0114632 entitled "Stabilized Active Halogen Solutions" to Janek et al., which is hereby incorporated by reference. One particularly useful compound is sulfamic acid. Sulfamic acid may function as both the acid component and the stabilizer since sulfamic acid has the stabilizer moiety N—H in the structure. Without the stabilizer or stabilizer moiety, the addition of the acid to the active halogen-containing solution could result in the generation of halogen gas.

Generally, the stabilizer is added to the active halogen-containing solution to further provide stability to the active halogen-containing solution. It is believed that stabilizer should be added in an amount of about 0.2 moles to about 2.0 moles of the N-hydrogen compound per mole of active halogen in the active halogen-containing solution and is typically added in an amount of about 0.4 moles to about 1.25 moles of the N-hydrogen compound per mole of active halogen in the active halogen-containing solution. More typically, there is about 0.5 moles to about 1.0 moles of the N-hydrogen compound per mole of the active halogen. When the N-hydrogen stabilizer compound has two N—H groups per molecule, then the molar ratio is closer to 0.5, and when the active N-hydrogen compound has only one N—H group, then the stabilizer present at a molar ratio closer to 1.0. It is noted that more or less of the stabilizer may be used, without departing from the scope of the invention, provided that stabilizing effect is achieved.

When sulfamic acid is added to the active halogen-containing component as the stabilizer, it is added in an amount that will not reduce the pH of the active-containing component below a pH of 9.0. Therefore, it is possible that the active halogen-containing component may contain an acidic compound. However, this acidic compound is distinct from the acidic component which is added to reduce the pH of the active halogen-containing component, even though the acid compound in the active halogen-containing component is the same as the acid in the acidic component.

The addition of the stabilizer also serves to improve the shelf life of the antimicrobial composition once prepared. The stabilizer serves to reduce the rate in which the activity of the active halogen, in the active halogen-containing compound alone or in solution, is diminished over time. Further, it is also believed that the stabilizer contributes to the low overall odor of the resulting compositions, versus the active halogen-containing compound in a solution at an elevated pH.

In one particular embodiment, the stabilizer is combined with the active halogen-containing component, prior to the addition of the acidic component. In this embodiment, the active halogen-containing component is part of a "stabilized active halogen-containing component", or a "stabilized active halogen containing solution", in the case of the active halogen containing component is part of a solution, each having an elevated pH. By "elevated pH" it is intended that the solution has a pH in the basic range, generally above a pH of about 9.0. Typically, stabilized active halogen solutions need to have an elevated pH to provide acceptable stability of the solution during production and storage. Not wishing to be bound by theory, but it is believed that the elevated pH minimizes the formation of the acid forms of the contained hypohalites thus slowing the disproportionation reaction of the acid forms, which is generally the primary route of decomposition. As such, stabilized active halogen solutions thus are prepared at elevated pH, typically a pH greater than about 10.0 or more.

The stabilized active halogen-containing solution also typically contains a stabilizer component which functions as a complexing agent. The stabilizer components described above may be used. One particularly effective stabilizer component for the active halogen-containing solutions is sulfamic acid, which has the ability to complex with the halogen to stabilize the halogen in solution. Sulfamic acid serves as stabilizer for the halogens in the solution. It is noted that the amount of the sulfamic acid added to the active halogen-containing solution for the purposes of stabilization does not reduce the pH out of the elevated range. In forming stabilized active halogen-containing solutions, generally the first step is to disperse the stabilizer component into an aqueous solution. As such, water is also a component of the stabilized active halogen-containing solution.

To form an active halogen-containing component, first an elevated pH solution is formed. Generally the aqueous solution with an elevated pH contains of a stabilizer, for example sulfamic acid and, an alkali or alkaline metal containing basic compound. Examples of suitable alkali or alkaline metal salts include, but not limited to, for example alkali and alkaline carbonates, bicarbonates, oxides and hydroxide. Particularly useful are sodium hydroxide and potassium hydroxide, which will form a sulfamate salt of the sulfamic acid. The basic compound is added in excess, which causes the pH of the resulting solution to be elevated.

Once the elevated pH solution is formed, the halogen source is added to the solution which results in the stabilized halogen-containing solution having an elevated pH. The stabilized active halogen-containing solutions will generally be a concentrated active halogen-containing solution, having a halogen content well above the typical concentration needed for disinfecting. Typically, the pH of the stabilized halogen-containing solution is about 9.0 or above, more typically 9.5 or above and most typically about 10.0 or above.

Other methods known in the art to form stabilized active halogen-containing solutions may also be used, including the methods described in various patents such as U.S. Pat. Nos. 5,942,126; 6,007,726; 5,683,654; 6,123,870; 6,136,205; 6,669,904; 6,660,307; 6,423,267; 6,156,229; 7,045,153; 7,309,503; and 7,045,153 and, 6,068,861; 6,299,909; 6,306,441; 6,322,822; 6,652,889; 6,551,624; 6,511,682; 6,506,418; 6,495,169; 6,375,991; 6,352,725; 6,348,219; and 6,322,822; each of the above US patents is hereby incorporated by references in their entirety. In addition, commercially available stabilized active halogen-containing solutions Stabrex® from Nalco Inc; BromMax® from Enviro Tech Chemicals; Stabrom® from Albemarle and Justeq, available from Justeq, LLC.

Generally, the antimicrobial composition will be provided as a two-part system. This is because the activity of the antimicrobial composition diminishes with time once the acidic component is added to the active halogen-containing component. By providing the composition in two separate parts, the acidification of the active halogen-containing component can occur just prior to use. In this manner, the overall efficacy will be maintained during use. Typically, once both parts are combined, the antimicrobial composition will have efficacy for about 7-30 days.

The two parts of the two-part system will include Part A, which contains the active halogen-containing component, and Part B, which contains the acidic component. The stabilizer, when used, may be present in either Part A or Part B. When the two parts are combined, the resulting composition will have a resulting pH 8.0 or lower. This two part system can be delivered for mixing at the point of use by either the provision of two distinct products, or using specialized packaging that separates the two parts until the contents are applied, or provision of two separate products for use in an automated diluting device that meters in the proper amount of each part into a receiving container. In addition to providing the desired pH, the two part system can also be used to adjust the active halogen concentration to the desired level.

Suitable two-part systems may include ready to use (RTU) solutions, where the two parts are mixed together and the resulting composition has the desired concentration of the active halogen and pH; or dilutable solutions where the two parts are mixed together to form a concentrated solution that needs to be diluted with water prior to use. Typically RTU solutions may be prepared by mixing two liquids together, or adding a solid to a liquid. The RTU solutions may be provided in two separate containers or may be provided in a single container with a removable or breakable separator means that allows the two parts of the composition to be mixed together. Alternatively, an RTU solution may formed by drawing portions of Part A from one part of a container and a complementary portion from another part of the same container as the composition is released from the container. In another embodiment, the RTU solution is prepared by having Part A and Part B drawn from a bulk container via an automated dilution device that meters out appropriate amounts of each part to obtain a ready to use solution. An exemplary means would be a spray means that mixes the parts in appropriate ratios prior to release from the container. For example, Part A and Part B may be mixed in the spray head prior to release form the container.

Another two-part system may form a solution which is concentrated and needs to be diluted prior to use. These are referred to as dilutable solutions. Dilutable solutions are solutions where the two parts are mixed together to form a concentrated solution and additional ingredients, such as water need to be mixed with the solution prior to use to ensure that the composition has the appropriate concentration prior to use. Dilutable solutions can be in the form of two separate containers of Part A and Part B that are added to a third container containing water. Alternative dilutable solutions can be formed where one of the Parts is first diluted with water prior to mixing with the other part. For example, if Part B is a concentrated solution, the concentrated solution is first diluted with an appropriate amount of water prior to addition to Part A. Another example is, if Part A and/or Part B is a solid, such as a powder or tablet, the powder or tablet is generally first dissolved in water prior to addition of the complementary part. When a solid is used, the solid may be placed in a water soluble pouch, a foil pouch, a sachet or a plastic container. Dilutable solutions may be made by using an automated dilution device which meters out appropriate amounts of each Part A and Part B from bulk containers into a delivery container, which is mixed with water that is present in the delivery or final use container, or with water that is added to the delivery or final use container as Part A and Part B are being added to the container or with water that is added after Part A and Part B are added to the delivery or final use container. The particular method the antimicrobial composition is prepared from Part A and Part B in not critical to the present invention, so long as the resulting composition has sufficient concentration of the active halogen and the pH is 8.0 or below.

In addition to the above components described herein, other additives, such as buffers, corrosion inhibitors, surfactants, chelators, builders, dyes and/or fragrances and the like, may be added.

The antimicrobial composition can be delivered to a surface to be cleaned, sanitized or disinfected by conventional means such as pouring the composition on a surface, a spray, which is applied to a surface via a spray means, including but not limited to, pump spray applicators, pressurized spray applicators and the like; a saturated wipe; a rag and a bucket; a mop and bucket; a sponge and a bucket; or via automated cleaning equipment and other similar and conventional ways to apply an antimicrobial composition to a surface for the purposes of sanitizing or disinfecting the surface.

Another possible means of application is preparation of ready to use solutions at the point of manufacture of the stabilized active halogen solution in combination with the acid at the desired active halogen concentration. Such solutions can be provided as the solution by itself or in combination with a wipe substrate. Alternatively, saturated wipes can be prepared by saturating wipes in a container with a antimicrobial solution made just prior to saturation in the wipe substrate. Suitable wipe substrates include woven and nonwoven materials. Nonwoven materials can be meltblown, coform, spunbond, airlaid, hydroentangled nonwovens, spunlace, bonded carded webs, and laminates thereof. The fibers used to prepare the wipe substrate may be cellulosic fiber, thermoplastic fibers and mixtures thereof. The fibers may also be continuous fibers, discontinuous fibers, staple fibers and mixtures thereof.

To use the antimicrobial composition of the present invention, a surface is treated with the substrate by spraying, pouring, wiping or otherwise applying the antimicrobial composition to the surface. Once applied to the surface, the antimicrobial composition is allowed to remain on the surface for a period of time. The antimicrobial composition may be applied to the surface and allowed to dry or may alternatively be dried by wiping the surface with a dry wipe or wiping device.

Active halogen-containing compounds and active halogen-containing compound solutions having an elevated pH, while being sufficient for water treatment applications, have been found to be insufficient to achieve hygienic disinfection targets, when used as provided at the elevated pH. Further, it has been discovered that dilution of stabilized active halogen products into water is also ineffective in achieving sporicidal efficacy. At typical levels of active ingredient concentrations that are generally found in disinfectants, diluted active halogen products have been found not to be effective as sporicidal composition alone. However, it has been discovered that the efficacy of active halogen-containing compounds and solutions containing the active-halogen containing compound can be sufficiently enhanced for utility in hygienic disinfection applications by reducing the pH through acidification. It has been discovered that lowering the pH of the halogen-containing solutions, in particular stabilized active halogen-containing solutions, (a solution containing a stabilizer as described above) by the addition of an acidic component to adjust the pH level to about 8.0 or less of the resulting composition, results in a composition having disinfecting efficacy, and, particularly a composition having sporicidal efficacy. As such, the antimicrobial composition described herein is especially effective as a disinfectant solution used to kill C. diff. spores. Not only does the acidified solution of stabilized active halogen achieve enhanced efficacy desired for sporicidal applications, the acidified application also has additional advantages of having a reduced odor, as compared to currently available sporicidal compositions. It has also been discovered that the compositions of the present invention also have an enhanced ability to pass the use dilution test.

The antimicrobial composition of the present invention has utility as a disinfecting composition. The antimicrobial composition has a special utility when used in locations where C. diff may be present including in health care facilities, such as doctor's offices, operating rooms, hospital rooms, emergency rooms, urgent care facilities and the like. The composition may also be used in veterinary facilities, daycare facilities, nursing homes and other similar locations where disinfecting or surfaces is necessary.

Other properties provided by the antimicrobial composition of the present invention may also include that the composition is generally compatible with floor finishes and will not remove such finishes. In addition, the composition generally leaves a low residue on the surface treated and generally does not streak on hard surfaces.

The following examples are intended to provide a more complete understanding of the present invention. Such a more complete understanding can be obtained by referring to the following illustrative examples of the practice of the invention. The examples are not intended, however, to limit the invention.

Example 1

The effect of pH reduction on the activity of stabilized bromine solutions on the spore form of *Clostridium difficile* (ATCC 43598) was determined using the EPA Standard Quantitative Disk Carrier Test Method at a contact time of 10 minutes at 20° C. An effective sporicide provides greater than 6 log reduction in the spore concentration.

As shown in Table 1, dilutions of as received stabilized bromine solutions to a concentration of 5,000-12,000 ppm total active halogen as $Cl_2$, produce solutions of high pH>12 which are ineffective. Stabrex® 20 is a stabilized bromine containing solution having a pH of about 13 and containing about 14% active bromine and is available from Nalco, having an office at 1601 W. Diehl Road, Naperville, Ill. 60563-1198. BromMax® 7.1 is a stabilized bromine containing solution containing sulfamic acid and sodium hydroxide having pH of about 13 and containing between about 16% active bromine and is made in accordance with U.S. Pat. Nos. 7,045,153 and 7,455,859, which are hereby incorporated by reference it their entirety. BromMax® 7.1 is available from Enviro Tech Chemicals, having an office at 500 Winmoore Way, Modesto, Calif. 95358.

The addition of an acid during dilution to reduce the pH to 8 or less produces a solution that is more effective as the stabilized bromine solutions alone as demonstrated by the >6 log reduction observed at pH 8.0 for a 6000 ppm solution and a <6 log reduction observed for a 12,000 ppm solution at an unmodified pH of 12.0.

TABLE 1

Effect of pH Modification on efficacy of stabilized bromine solutions

| Ref. | Stabilized Bromine Product | pH modification by acid addition | Test pH | Total active halogen (ppm as $Cl_2$) | Log reduction | Log reduction summary |
|---|---|---|---|---|---|---|
| 1 | Stabrex ® 20 | No | 12.2 | 5,000 | 5.56 | <6 |
| 2 | Stabrex ® 20 | No | 12.3 | 6,000 | 5.23 | <6 |
| 3 | Stabrex ® 20 | No | 12.6 | 9,000 | 5.93 | <6 |
| 4 | Stabrex ® 20 | No | 12.8 | 12,000 | 4.86 | <6 |
| 5 | BromMax ® 7.1 | No | 12.6 | 12,000 | 4.83 | <6 |
| 6 | Stabrex ® 20 | Yes (HCl) | 9.0 | 6,000 | 5.79 | <6 |
| 7 | Bromax ® 7.1 | Yes (HCl) | 8.0 | 6,000 | 6.97 | >6 |

Example 2

The effect of pH reduction on the activity of two types of stabilized bromine solutions on the spore form of *Clostridium difficile* (ATCC 43598) was determined using the EPA Standard Quantitative Disk Carrier Test Method at a contact time of 10 minutes at 20° C. An effective sporicide provides a >6 log reduction in the spore concentration.

As shown in Table 2. both Stabrex® and BromMax® solutions provided >6 log reductions at reduced pH. This demonstrates that the enhanced efficacy effect of pH reduction can be achieved for a variety of stabilized bromine sources.

TABLE 2

Effect of pH Modification on efficacy of stabilized bromine solutions

| Ref. | Stabilized Bromine Product | pH modification by acid addition | Test pH | Total active halogen (ppm as $Cl_2$) | Log reduction | Log reduction summary |
|---|---|---|---|---|---|---|
| 8 | BromMax ® 7.1 | Yes (HCl) | 1.9 | 6,000 | >6.78 | >6 |
| 9 | Stabrex ® 20 | Yes (HCl) | 4.8 | 6,000 | 6.10 | >6 |
| 10 | BromMax ® 7.1 | Yes (Sulfamic) | 1.6 | 6,000 | 6.8 | >6 |

Example 3

The stability of diluted solutions of stabilized bromine with and without acid addition were determined by dilution of stabilized active bromine products as shown in Table 3, to a theoretical concentration of ~6,000 ppm total active halogen, storage at 20° C. and measuring the total active halogen concentration and pH as function of time. Total active halogen concentrations reported as $Cl_2$ were measured using standard DPD methodology.

TABLE 3

Stability test formulations

| | Part A | Part B | |
|---|---|---|---|
| Ref. | Stabilized Bromine | Water | Acid |
| 11 | 8.5 grams of BromMax ® 7.1 | 91.5 grams of D.I water | None |
| 12 | 9.4 grams of Stabrex ® 20 | 90.6 grams of D.I water | None |
| 8 | 8.5 grams of BromMax ® 7.1 | 89.8 grams of D.I water | 1.7 grams Hydrochloric Acid (37%) |
| 9 | 9.4 grams of Stabrex ® 20 | 88.9 grams of D.I water | 1.2 grams Hydrochloric Acid (37%) |
| 13 | 8.5 grams of BromMax ® 7.1 | 89.8 grams of D.I water | 1.7 grams Citric Acid |
| 14 | 8.5 grams of BromMax ® 7.1 | 88.5 grams of D.I water | 3.0 grams Boric Acid |
| 10 | 8.5 grams of BromMax ® 7.1 | 89.2 grams of D.I water | 2.3 grams Sulfamic Acid |
| 15 | 8.5 grams of BromMax ® 7.1 | 88.8 grams of D.I water | 2.7 grams Sodium Bisulfate |
| 16 | 8.5 grams of BromMax ® 7.1 | 88.5 grams of D.I water | 3.0 grams Sodium Bicarbonate |

It is desirable that after dilution, solutions remain stable for a minimum of 1 hour for immediate use, 1 day for industrial applications or up to 1 week for institutional applications. As shown in Table 4, acidified dilutions provide sufficient stability for practical application as >80% of the active halogen remains even after 7 days. As shown in Table 5 acidified solutions not only retained high levels of active halogen they also remained as desired at reduced pH.

TABLE 4

Effect of pH modification on active storage stability of stabilized bromine solutions (active halogen concentration).

| | | | % of added (~6000 ppm) active halogen remaining as a function of time | | | | |
|---|---|---|---|---|---|---|---|
| Ref. | Stabilized Bromine Product | pH modification by acid addition | Initial pH | 1 hour | 1 day | 7 days | 14 days | 21 days |
| 8 | BromMax ® 7.1 | Yes (HCl) | 1.9 | 91.5 | 89.3 | 87.9 | 85.3 | 77.3 |
| 9 | Stabrex ® 20 | Yes (HCl) | 4.8 | 100 | 93.6 | 98.5 | 95.3 | 86.8 |
| 13 | BromMax ® 7.1 | Yes (Citric) | 3.8 | 91.1 | 84.0 | 83.8 | 76.5 | 63.6 |
| 11 | BromMax ® 7.1 | No | 11.2 | 70 | 45.8 | 43.8 | 43.9 | 44.0 |
| 12 | Stabrex ® 20 | No | 12.6 | 100 | 93.6 | 80.3 | 75.5 | |
| 14 | BromMax ® 7.1 | Yes (Boric) | 7.6 | 88.1 | 92.9 | 87.1 | | |
| 10 | BromMax ® 7.1 | Yes (sulfamic) | 1.6 | 98.1 | 94.7 | 81.8 | | |
| 15 | BromMax ® 7.1 | Yes (sodium bisulfate) | 2.4 | 90.5 | 91.2 | 94.3 | | |
| 16 | BromMax ® 7.1 | Yes (sodium bicarbonate) | 8.6 | 97.1 | 84.8 | 84.6 | | |

TABLE 5

Effect of pH modification on active storage stability of stabilized bromine solutions (pH).

| Ref. | Stabilized Bromine product | pH modification by acid addition | Initial | 7 days | 14 days | 21 days |
|---|---|---|---|---|---|---|
| 8 | BromMax ® 7.1 | Yes (HCl) | 1.8 | 1.8 | — | 1.8 |
| 9 | Stabrex ® 20 | Yes (HCl) | 4.8 | 3.8 | — | 2.3 |
| 13 | BromMax ® 7.1 | Yes (Citric) | 3.8 | 4.6 | — | 4.1 |
| 11 | BromMax ® 7.1 | No | 11.2 | 11.2 | 11.2 | 11.1 |
| 10 | BromMax ® 7.1 | Yes (sulfamic) | 1.6 | 1.5 | — | — |
| 15 | BromMax ® 7.1 | Yes (sodium bisulfate) | 2.5 | 2.0 | — | — |
| 16 | BromMax ® 7.1 | Yes (sodium bicarbonate) | 8.6 | 8.5 | — | — |

Example 4

The odor profiles of potential sporicidal solutions were determined using fifteen panellists to rate the odor of the test solutions using a score for Odor intensity (0=no odor, 10=very strong Odor) and Odor pleasantness (0=Very Pleasant, 10=Very Unpleasant).

As shown in Table 6, stabilized bromine provided a lower and less noxious odor than other materials utilized as sporicides.

TABLE 6

Odor profiles of potential disinfectants

| Material | Odor Intensity | Odor Pleasantness |
|---|---|---|
| Stabilized Bromine @ 6000 ppm | 1.1 | 2.9 |
| Sodium Hypochlorite @ 6000 ppm | 4.2 | 4.7 |
| Peracetic Acid @ 4000 ppm | 7.5 | 7.5 |

Example 5

An acidified solution of stabilized active halogen solution containing active bromine was produced by combining: Part A, commercial grade sodium hypochlorite and Part B, a mixture of sulfamic acid and sodium bromide. Generation of an acidified stabilized active halogen solution was demonstrated by the observation of a reduced pH (relative to commercial NaOCl) and a stable target active halogen concentration.

A 10 g portion of Part A, commercial "6%" sodium hypochlorite solution (Clorox) was added to 90 grams of Part B, an aqueous solution containing 1.9 grams of aqueous 46% NaBr and 0.82 g sulfamic acid (SA). The initial pH of Part A solution was >12.0, and the initial pH of solution Part B was 1.1. Active halogen concentrations were measured using standard DPD methodology. As shown in Table 7, an acidified stabilized active halogen solution was produced containing ~8000 ppm total active halogen and 4000 ppm free active halogen. Acidification was demonstrated by observation of a pH of 8.5-8.9 which is significantly lower than the pH of 10.3 observed for a simple 1:10 dilution of Part A into deionized water. Active bromine generation was demonstrated by the observation of a significant concentration of free active halogen and the presence of a yellow color.

TABLE 7

Acidified stabilized active halogen solution composition: 1 NaOCl + (1 NaBr + 1 SA)

| Delta Time from mixing (min) | pH | Temperature (° C.) | Total active halogen (ppm as $Cl_2$) | Free active halogen (ppm as $Cl_2$) | Color |
|---|---|---|---|---|---|
| 2 | 8.9 | 24 | 8720 | 3560 | yellow |
| 30 | 8.5 | 23 | 7920 | 4480 | yellow |

Example 6

An acidified solution of stabilized active halogen-containing active bromine was produced by combining: Part A, commercial grade sodium hypochlorite and Part B, a mixture of sulfamic acid and sodium bromide. Generation of an acidified stabilized active halogen solution was demonstrated by the observation of a reduced pH (relative to commercial NaOCl) and a stable target active halogen concentration.

A 10 g portion of Part A, commercial "6%" sodium hypochlorite solution (Clorox) was added to 90 grams of Part B, an aqueous solution containing 1.9 grams of aqueous 46% NaBr and 1.64 g sulfamic acid (SA). The initial pH of Part A solution was >12.0, and the initial pH of solution Part B was <1.0. Active halogen concentrations were measured using standard DPD methodology.

As shown in Table 8, an acidified stabilized active halogen solution was produced containing ~10,000 ppm total active halogen and 8000 ppm free active halogen. Acidification was demonstrated by observation of a pH of 0.4-0.5 which is significantly lower than the pH of 10.3 observed for a simple 1:10 dilution of Part A into deionized water. Active bromine generation was demonstrated by the observation of a significant concentration of free active halogen and the presence of a yellow color.

TABLE 8

Acidified stabilized active halogen solution composition: 1 NaOCl + (1 NaBr + 2 SA)

| Delta Time from mixing (min) | pH | Temperature (° C.) | Total active halogen (ppm as $Cl_2$) | Free active halogen (ppm as $Cl_2$) | Color |
|---|---|---|---|---|---|
| 2 | 0.4 | 24 | 10120 | 8200 | Yellow |
| 15 | 0.5 | 23 | — | — | — |
| 30 | — | — | 9880 | 7800 | Yellow |

Example 7

An acidified solution of stabilized active halogen-containing active chlorine was produced by combining: Part A, commercial grade sodium hypochlorite and Part B, aqueous sulfamic acid. Generation of an acidified stabilized active halogen solution was demonstrated by the observation of a reduced pH (relative to commercial NaOCl) and a stable target active halogen concentration.

A 10 g portion of Part A, commercial "6%" sodium hypochlorite solution (Clorox) was added to 90 grams of Part B, an aqueous solution containing 1.64 g sulfamic acid (SA). The initial pH of Part A solution was >12.0, and the initial pH of solution Part B was <1.0. Active halogen concentrations were measure using standard DPD methodology.

TABLE 9

Acidified stabilized active halogen solution composition:
1 NaOCl + (2 SA)

| Delta Time from mixing (min) | pH | Temperature (° C.) | Total active halogen (ppm as Cl₂) | Free active halogen (ppm as Cl₂) | Color |
|---|---|---|---|---|---|
| 2 | 0.8 | 25 | 6480 | 680 | No color |
| 13 | 0.96 | 23 | — | — | — |

Example 8

The following example shows the rapid speed of kill of a composition within the scope of the present invention. An antimicrobial composition was prepared by combining sulfamic acid with a stabilized active halogen containing solution (BromMax® 7.1) to obtain a pH of <4.0.

The resulting acidified solution was tested for *Clostridium difficile* efficacy as described in Example 1. As shown in Table 10, greater than 6 log reductions were observed at contact times of 3 minutes and greater.

TABLE 10

Effect of time on *C. difficile* efficacy of acidified stabilized bromine solutions

| Contact Time (min) | Total Active Halogen (ppm as Cl2) | Log Reduction | Passing Criteria |
|---|---|---|---|
| 10 | 6000 ppm | 6.8 | >6 (Pass) |
| 5 | 6000 ppm | 7.2 | >6 (Pass) |
| 3 | 6000 ppm | 7.1 | >6 (Pass) |
| 1 | 6000 ppm | 2.7 | >6 (Fail) |

Example 9

The following example show an enhanced efficacy against non-spore forming bacteria. An antimicrobial composition was prepared by combining sulfamic acid (Part B) with a stabilized active halogen containing solution (Part A) (BromMax® 7.1) to obtain a pH of <4.0.

The resulting solution was tested for efficacy against *P. aeruginosa* and *S. aureus* using AOAC use dilution test (UDT) methodology at 5 minutes contact time.

By this method it is desirable to have <2 tubes showing growth at the end of the challenge. As shown in Table 11, the acidified solution provided significantly greater efficacy than the unacidified Part A alone.

TABLE 11

Effect of acidification on stabilized bromine efficacy at 5 minute contact.

| Composition | Total Active Halogen (ppm as Cl2) | Organism | # of tubes showing Growth out of 60 |
|---|---|---|---|
| Part A | 6000 | P. aeruginosa | 4/60 |
| Part A and B | 6000 | P. aeruginosa | 1/60 |
| Part A and B | 6000 | S. aureus | 0/60 |

As rapid kill is desirable, efficacy was also determined at 3 minute contact time. As shown in Table 12, efficacy targets were achieved at 3 minutes as well.

TABLE 12

Efficacy of acidified stabilized bromine at 3 minute contact in triplicate.

| Composition | Total Active Halogen (ppm as Cl2) | Organism | # of tubes showing Growth out of 60 |
|---|---|---|---|
| Part A and B | 6000 | P. aeruginosa ATCC 15442 | 0/60 |
| Part A and B | 6000 | S. aureus ATCC 6538 | 0/60 |
| Part A and B | 6000 | P. aeruginosa ATCC 15442 | 1/60 |
| Part A and B | 6000 | S. aureus ATCC 6538 | 0/60 |
| Part A and B | 6000 | P. aeruginosa ATCC 15442 | 0/60 |
| Part A and B | 6000 | S. aureus ATCC 6538 | 0/60 |

Using the AOAC Germicidal Spray Test (GST), an even more rapid (1 minute) contact time was achieved.

TABLE 13

AOAC Germicidal Spray Test (GST).

| Composition | Total Active Halogen (ppm as Cl2) | Organism | # of tubes showing Growth out of 10 |
|---|---|---|---|
| Part A and B | 6000 | K. pneumonia ATCC 4352 | 0/10 |
| Part A and B | 6000 | S. enterica ATCC 10708 | 0/10 |
| Part A and B | 6000 | VRE ATCC 51575 | 0/10 |
| Part A and B | 6000 | A. baumannii ATCC 19606 | 0/10 |
| Part A and B | 6000 | MRSA ATCC 33592 | 0/10 |
| Part A and B | 6000 | P. aeruginosa ATCC 15442 | 0/10 |
| Part A and B | 6000 | S. aureus ATCC 6538 | 0/10 |

Example 10

The following example shows that the composition possesses a low odor as compared to other commercial products. The acidified stabilized active halogen containing antimicrobial composition was prepared by combining sulfamic acid (Part B) with a stabilized active halogen containing solution (Part A) (BromMax® 7.1) to obtain a pH of <4.0.

The odor of this material was evaluated against commercially available sporicides by the following method. Card board boxes (12 inch×12 inch) were lined with plastic. Two of four the top flaps are cut off. A hole, 4 inches×1¾" is cut in one of the remaining top flaps. The cut out piece from the hole is then taped along one of the edges so that it covers the hole, yet can be lifted up in order to allow odor evaluation A 12"×11" vinyl tile is placed in the bottom of the box. 10 grams of diluted finished product is absorbed onto a laboratory paper towel. The tile in the bottom of the box is wiped down with the paper towel. The paper towel is left inside the box and the top of the box is sealed with tape.

Panelists were then asked to rank the odor in the based on both strength of odor from 0 to 10 with 0 being no odor and 10 being a very strong odor, as well as for pleasantness of odor, where 0 is very pleasant and 10 being very unpleasant/objectionable.

As shown in Table 14 the odor profile of the acidified stabilized active halogen composition was significantly better than the commercial benchmarks.

TABLE 14

Odor comparison of sporicidal materials

| Composition | Odor Strength | Odor pleasantness |
|---|---|---|
| Part A and B | 1.7 | 3.7 |
| Clorox Ultra Bleach 1:10 Dilution | 4.3 | 5.4 |
| Clorox Dispatch RTU | 5.3 | 5.1 |
| Virasept (Ecolab) | 6.4 | 5.1 |

The use of stabilized active halogen solutions for the treatment of industrial cooling waters is well known. Such products are typically used as provided and applied at relatively low concentrations to achieve biocidal control of vegetative microbiological species. However, the use of active halogen solution which has been acidified has not been taught in the art, as shown in the foregoing examples.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

We claim:

1. An antimicrobial composition comprising,
   a a stabilized, active halogen-containing component with anti-microbial activity, the active halogen-containing component is active bromine and the active halogen-containing component has a pH of above about 9, the active halogen-containing component comprises a basic component and a stabilizing amount of a stabilizer comprising a N—H containing compound, and wherein the stabilizer does not reduce the pH of the active halogen-containing component below 9.0; and
   b an acidic component comprising a strong acid selected from the group consisting of hydrochloric acid, nitric acid, sulfuric acid, sulfamic acid and combinations thereof;
   wherein the strong acid is an amount, in addition to the stabilizing amount, that provides the composition with a pH of about 8 or lower and increases the antimicrobial activity of the active halogen, and
   wherein the antimicrobial composition exhibits a $\text{Log}_{10}$ kill rate of $\geq 6$.

2. The antimicrobial composition according to claim 1, wherein the $\text{Log}_{10}$ kill rate of $\geq 6$ is achieved with a contact time of 3 minutes or greater.

3. The antimicrobial composition according to claim 2, wherein the contact time is 10 minutes or less.

4. The antimicrobial composition according to claim 1, wherein the acidic component is added in an amount to lower the pH of the antimicrobial composition to 7.0 or below.

5. The antimicrobial composition according to claim 4, wherein the acidic component is added in an amount to lower the pH of the antimicrobial composition to 3.0 or below.

6. The antimicrobial composition according to claim 1, wherein the acidic component has a pH of less than about 3.

7. The antimicrobial composition according to claim 1, wherein the stabilizer being the N—H containing compound comprises sulfamic acid.

8. The antimicrobial composition according to claim 1, wherein the stabilizer comprises sulfamic acid and the active halogen-containing component further includes active chlorine.

9. The antimicrobial composition according to claim 8, wherein the $\text{Log}_{10}$ kill rate of $\geq 6$ is achieved with a contact time of 3 minutes or greater.

10. The antimicrobial composition according to claim 8, wherein the contact time is 10 minutes or less.

11. The antimicrobial composition according to claim 8, wherein the acidic component is added in an amount to lower the pH of the antimicrobial composition to 7 or below.

12. The antimicrobial composition according to claim 11, wherein the acidic component is added in an amount to lower the pH of the antimicrobial composition to 3 or below.

13. The antimicrobial composition according to claim 1, where the total active halogen concentration in the composition is between about 25 and about 60,000 ppm on a $Cl_2$ equivalent basis.

14. The antimicrobial composition according to claim 13, wherein the total active halogen concentration in the composition is between about 50 and about 12,000 ppm on a $Cl_2$ equivalent basis.

15. The antimicrobial composition according to claim 14, wherein the total active halogen concentration in the composition is between about 500 and 10,000 ppm on a $Cl_2$ equivalent basis.

16. The antimicrobial composition according to claim 15, wherein the total active halogen concentration in the composition is between about 4,000 and 8,000 ppm on a $Cl_2$ equivalent basis.

17. A two-part antimicrobial composition comprising
   a a first part comprising a stabilized, active halogen-containing solution containing a source of an active halogen with anti-microbial activity, wherein the active halogen is active bromine and comprises an elevated pH of above about 9, the active halogen-containing solution comprises a basic component and a stabilizing amount of a stabilizer comprising a N—H containing compound, and wherein the stabilizer does not reduce the pH of the active halogen-containing component below 9.0; and
   b a second part comprising an acidic component comprising a strong acid selected from the group consisting of hydrochloric acid, nitric acid, sulfuric acid, sulfamic acid and combinations thereof;
   wherein the first part and the second part are kept separate from each other during storage and the first part and the second part are mixed together just prior to use to obtain an antimicrobial composition,
   wherein the strong acid is an amount in addition to the stabilizing amount, that provides the composition with a pH of about 8 or lower and increases the antimicrobial activity of the active halogen, and
   wherein the antimicrobial composition, formed when the first and second parts are combined, exhibits a $\text{Log}_{10}$ kill rate of $\geq 6$.

18. The two-part antimicrobial composition according to claim 17, wherein the stabilizer being the N—H containing compound comprises sulfamic acid.

19. The two-part antimicrobial composition according to claim 17, wherein the elevated pH is a pH greater than 9.0.

20. The two part antimicrobial composition according to claim 17, wherein the acidic component has a pH of less than 3.

21. The two-part antimicrobial composition according to claim 17, wherein the first part is provided in a first container and the second part is provided in second container and the amount of the first part in the first container and the amount of the second part in the second container are proportional such that the entire contents of both containers are mixed together to form an antimicrobial composition.

22. The two-part antimicrobial composition according to claim 17, wherein the first part and the second part are in a single container, wherein the first part is separated from the second part in the container by a separator.

23. The two-part antimicrobial composition according to claim 22, wherein the separator is removable from the container or movable in the container to allow the first part and the second part can mix together.

24. The two-part antimicrobial composition according to claim 22, wherein the container further comprises a spray head and the first part and the second part are mixed in the spray head.

25. The two-part antimicrobial composition according to claim 17, wherein the first part is provided in a first container and the second part is provided in second container, wherein a portion of the contents of the first container are mixed with a portion of the contents of the second container to form the antimicrobial composition.

26. The two-part antimicrobial composition according to claim 17, further comprising water to dilute the two components once combined.

27. A wipe comprising the antimicrobial composition according to claim 1.

28. A method of disinfecting a surface comprising applying the antimicrobial composition according to claim 1 to the surface.

29. A method of controlling spores on a surface comprising applying the composition according to claim 1 to the surface.

* * * * *